US007919075B1

(12) United States Patent
Michal et al.

(10) Patent No.: US 7,919,075 A0
(45) Date of Patent: Apr. 5, 2011

(54) COATINGS FOR IMPLANTABLE MEDICAL DEVICES

(75) Inventors: Eugene T. Michal, San Francisco, CA (US); Syed F. A. Hossainy, Fremont, CA (US); Ashok Shah, San Jose, CA (US)

(73) Assignee: Advanced Cardiovascular Systems, Inc., Santa Clara, CA (US)

(*) Notice: Subject to any disclaimer, the term of this patent is extended or adjusted under 35 U.S.C. 154(b) by 965 days.

(21) Appl. No.: 10/104,769

(22) Filed: Mar. 20, 2002

(51) Int. Cl.
A61K 31/74 (2006.01)
A61K 9/00 (2006.01)
A61F 2/00 (2006.01)
A01N 25/00 (2006.01)
A61F 2/06 (2006.01)

(52) U.S. Cl. ............ 424/78.03; 424/400; 424/423; 424/405; 623/1.42; 623/1.11; 623/1.45

(58) Field of Classification Search ......... 424/78.03, 424/400, 423, 405; 623/1.42, 1.11, 1.45
See application file for complete search history.

(56) References Cited

U.S. PATENT DOCUMENTS

| | | | |
|---|---|---|---|
| 3,844,527 A * | 10/1974 | Scott | 249/189 |
| 4,329,383 A | 5/1982 | Joh | 428/36 |
| 4,733,665 A | 3/1988 | Palmaz | 128/343 |
| 4,800,882 A | 1/1989 | Gianturco | 128/343 |
| 4,882,168 A | 11/1989 | Casey et al. | 424/468 |
| 4,886,062 A | 12/1989 | Wiktor | 128/343 |
| 4,941,870 A | 7/1990 | Okada et al. | 600/36 |
| 4,977,901 A | 12/1990 | Ofstead | 128/772 |
| 5,112,457 A | 5/1992 | Marchant | 204/165 |
| 5,165,919 A | 11/1992 | Sasaki et al. | 424/488 |
| 5,272,012 A | 12/1993 | Opolski | 428/423.1 |
| 5,292,516 A | 3/1994 | Viegas et al. | 424/423 |
| 5,298,260 A | 3/1994 | Viegas et al. | 424/486 |
| 5,300,295 A | 4/1994 | Viegas et al. | 424/427 |
| 5,306,501 A | 4/1994 | Viegas et al. | 424/423 |
| 5,328,471 A | 7/1994 | Slepian | 604/101.3 |
| 5,330,768 A | 7/1994 | Park et al. | 424/501 |
| 5,380,299 A | 1/1995 | Fearnot et al. | 604/265 |
| 5,417,981 A | 5/1995 | Endo et al. | 424/486 |
| 5,447,724 A | 9/1995 | Helmus et al. | 424/426 |
| 5,455,040 A | 10/1995 | Marchant | 424/426 |
| 5,462,990 A | 10/1995 | Hubbell et al. | 525/54.1 |
| 5,464,650 A | 11/1995 | Berg et al. | 427/2.3 |
| 5,569,463 A | 10/1996 | Helmus et al. | 424/426 |
| 5,578,073 A | 11/1996 | Haimovich et al. | 623/1 |
| 5,605,696 A | 2/1997 | Eury et al. | 424/423 |
| 5,609,629 A | 3/1997 | Fearnot et al. | 623/1 |
| 5,624,411 A | 4/1997 | Tuch | 604/265 |
| 5,628,730 A | 5/1997 | Shapland et al. | 604/21 |
| 5,649,977 A | 7/1997 | Campbell | 623/1 |
| 5,658,995 A | 8/1997 | Kohn et al. | 525/432 |
| 5,667,767 A | 9/1997 | Greff et al. | 424/9.411 |
| 5,670,558 A * | 9/1997 | Onishi et al. | 523/112 |
| 5,679,400 A | 10/1997 | Tuch | 427/2.14 |
| 5,700,286 A | 12/1997 | Tartaglia et al. | 623/1 |
| 5,702,754 A | 12/1997 | Zhong | 427/2.12 |
| 5,716,981 A | 2/1998 | Hunter et al. | 514/449 |
| 5,735,897 A | 4/1998 | Buirge | 623/12 |
| 5,746,998 A | 5/1998 | Torchilin et al. | 424/9.4 |
| 5,776,184 A | 7/1998 | Tuch | 623/1 |
| 5,788,979 A | 8/1998 | Alt et al. | 424/426 |
| 5,800,392 A | 9/1998 | Racchini | 604/96 |
| 5,820,917 A | 10/1998 | Tuch | 427/2.1 |
| 5,824,048 A | 10/1998 | Tuch | 623/1 |
| 5,824,049 A | 10/1998 | Ragheb et al. | 623/1 |
| 5,830,178 A | 11/1998 | Jones et al. | 604/49 |
| 5,837,008 A | 11/1998 | Berg et al. | 623/1 |
| 5,837,313 A | 11/1998 | Ding et al. | 427/2.21 |
| 5,851,508 A | 12/1998 | Greff et al. | 424/9.411 |
| 5,858,746 A | 1/1999 | Hubbell et al. | 435/177 |
| 5,865,814 A | 2/1999 | Tuch | 604/265 |
| 5,869,127 A | 2/1999 | Zhong | 427/2.12 |
| 5,873,904 A | 2/1999 | Ragheb et al. | 623/1 |
| 5,876,433 A | 3/1999 | Lunn | 623/1 |
| 5,877,224 A | 3/1999 | Brocchini et al. | 514/772.2 |
| 5,897,955 A | 4/1999 | Drumheller | 428/422 |
| 5,925,720 A | 7/1999 | Kataoka et al. | 525/523 |
| 5,955,509 A | 9/1999 | Webber et al. | 514/772.7 |
| 5,971,954 A | 10/1999 | Conway et al. | 604/96 |
| 5,980,928 A | 11/1999 | Terry | 424/427 |
| 5,980,972 A | 11/1999 | Ding | 427/2.24 |
| 5,997,517 A | 12/1999 | Whitbourne | 604/265 |
| 6,010,530 A | 1/2000 | Goicoechea | 623/1 |
| 6,015,541 A | 1/2000 | Greff et al. | 424/1.25 |

(Continued)

FOREIGN PATENT DOCUMENTS

EP    0 301 856    2/1989

(Continued)

OTHER PUBLICATIONS

Ramanathan et al., "Synthesis and Characterization of Polyurethane Microspheres," in Pure & Appl. Chem., vol. 70, No. 6, pp. 1295-1299, 1998).*
Pulfer et al., ("Incorporation of nitric oxide-releasing cross-linked polyethyleneimine microspheres into vascular grafts" in Journal of Biomedical Materials Research, vol. 37, Issue 2, pp. 182-189).*
Anonymous, *Cardiologists Draw—Up The Dream Stent*, Clinica 710:15 (Jun. 17, 1996), http://www.dialogweb.com/cgi/document?req=1061848202959, printed Aug. 25, 2003 (2 pages).
Anonymous, *Heparin-coated stents cut complications by 30%*, Clinica 732:17 (Nov. 18, 1996), http://www.dialogweb.com/cgi/document?reg=106184787153, printed Aug. 25, 2003 (2 pages).
Anonymous, *Rolling Therapeutic Agent Loading Device for Therapeutic Agent Delivery or Coated Stent* (Abstract 434009), Res. Disclos. pp. 974-975 (Jun. 2000).

(Continued)

*Primary Examiner* — Blessing M Fubara
(74) *Attorney, Agent, or Firm* — Squire Sanders & Dempsey (US) LLP

(57) ABSTRACT

Polymer coatings for medical devices are disclosed. The polymers can include at least one unit derived from ethylene and at least one vinyl unit or acrylic unit. The coatings can have a biologically compatible compound conjugated to, or blended with, the polymer.

48 Claims, No Drawings

U.S. PATENT DOCUMENTS

| | | | |
|---|---|---|---|
| 6,033,582 A | 3/2000 | Lee et al. | 216/37 |
| 6,042,875 A | 3/2000 | Ding et al. | 427/2.24 |
| 6,051,576 A | 4/2000 | Ashton et al. | 514/255 |
| 6,051,648 A | 4/2000 | Rhee et al. | 525/54.1 |
| 6,056,993 A | 5/2000 | Leidner et al. | 427/2.25 |
| 6,060,451 A | 5/2000 | DiMaio et al. | 514/13 |
| 6,060,518 A | 5/2000 | Kabanov et al. | 514/781 |
| 6,080,488 A | 6/2000 | Hostettler et al. | 428/423.3 |
| 6,096,070 A | 8/2000 | Ragheb et al. | 623/1 |
| 6,099,562 A | 8/2000 | Ding et al. | 623/1.46 |
| 6,110,188 A | 8/2000 | Narciso, Jr. | 606/153 |
| 6,110,483 A | 8/2000 | Whitbourne et al. | 424/423 |
| 6,113,629 A | 9/2000 | Ken | 623/1.1 |
| 6,120,536 A | 9/2000 | Ding et al. | 623/1.43 |
| 6,120,904 A | 9/2000 | Hostettler et al. | 428/423.3 |
| 6,121,027 A | 9/2000 | Clapper et al. | 435/180 |
| 6,129,761 A | 10/2000 | Hubbell | 623/1 |
| 6,153,252 A | 11/2000 | Hossainy et al. | 427/2.3 |
| 6,165,212 A | 12/2000 | Dereume et al. | 623/1.13 |
| 6,203,551 B1 | 3/2001 | Wu | 606/108 |
| 6,231,600 B1 | 5/2001 | Zhong | 623/1.42 |
| 6,231,852 B1* | 5/2001 | Bredesen | 424/94.4 |
| 6,232,336 B1* | 5/2001 | Hrabie et al. | 514/402 |
| 6,240,616 B1 | 6/2001 | Yan | 29/527.2 |
| 6,245,753 B1 | 6/2001 | Byun et al. | 514/56 |
| 6,251,136 B1 | 6/2001 | Guruwaiya et al. | 623/1.46 |
| 6,254,632 B1 | 7/2001 | Wu et al. | 623/1.15 |
| 6,258,121 B1 | 7/2001 | Yang et al. | 623/1.46 |
| 6,283,947 B1 | 9/2001 | Mirzaee | 604/264 |
| 6,283,949 B1 | 9/2001 | Roorda | 604/288.02 |
| 6,284,305 B1 | 9/2001 | Ding et al. | 427/2.28 |
| 6,287,628 B1 | 9/2001 | Hossainy et al. | 427/2.3 |
| 6,299,604 B1 | 10/2001 | Ragheb et al. | 604/265 |
| 6,306,176 B1 | 10/2001 | Whitbourne | 623/23.59 |
| 6,331,313 B1 | 12/2001 | Wong et al. | 424/427 |
| 6,335,029 B1 | 1/2002 | Kamath et al. | 424/423 |
| 6,346,110 B2 | 2/2002 | Wu | 606/108 |
| 6,358,556 B1 | 3/2002 | Ding et al. | 427/2.24 |
| 6,379,381 B1 | 4/2002 | Hossainy et al. | 623/1.42 |
| 6,379,691 B1* | 4/2002 | Tedeschi et al. | 424/423 |
| 6,387,379 B1* | 5/2002 | Goldberg et al. | 424/400 |
| 6,395,326 B1 | 5/2002 | Castro et al. | 427/2.24 |
| 6,419,692 B1 | 7/2002 | Yang et al. | 623/1.15 |
| 6,437,032 B1* | 8/2002 | Iyengar et al. | 524/197 |
| 6,451,373 B1 | 9/2002 | Hossainy et al. | 427/2.24 |
| 6,494,862 B1 | 12/2002 | Ray et al. | 604/96.01 |
| 6,503,556 B2 | 1/2003 | Harish et al. | 427/2.24 |
| 6,503,954 B1 | 1/2003 | Bhat et al. | 514/772.2 |
| 6,506,437 B1 | 1/2003 | Harish et al. | 427/2.25 |
| 6,527,801 B1 | 3/2003 | Dutta | 623/1.46 |
| 6,527,863 B1 | 3/2003 | Pacetti et al. | 118/500 |
| 6,540,776 B2 | 4/2003 | Millare et al. | 623/1.15 |
| 6,541,116 B2* | 4/2003 | Michal et al. | 428/420 |
| 6,544,223 B1 | 4/2003 | Kokish | 604/103.01 |
| 6,544,543 B1 | 4/2003 | Mandrusov et al. | 424/422 |
| 6,544,582 B1 | 4/2003 | Yoe | 427/2.24 |
| 6,555,157 B1 | 4/2003 | Hossainy | 427/2.24 |
| 6,558,733 B1 | 5/2003 | Hossainy et al. | 427/2.24 |
| 6,565,659 B1 | 5/2003 | Pacetti et al. | 118/500 |
| 6,572,644 B1 | 6/2003 | Moein | 623/1.11 |
| 6,585,765 B1 | 7/2003 | Hossainy et al. | 623/1.45 |
| 6,585,926 B1 | 7/2003 | Mirzaee | 264/400 |
| 6,605,154 B1 | 8/2003 | Villareal | 118/500 |
| 6,660,034 B1* | 12/2003 | Mandrusov et al. | 623/1.42 |
| 6,793,960 B1* | 9/2004 | Michal et al. | 427/2.24 |
| 6,908,624 B2* | 6/2005 | Hossainy et al. | 424/424 |
| 7,186,789 B2* | 3/2007 | Hossainy et al. | 528/272 |
| 7,202,325 B2* | 4/2007 | Pacetti et al. | 528/272 |
| 2001/0018469 A1 | 8/2001 | Chen et al. | 523/121 |
| 2001/0037145 A1 | 11/2001 | Guruwaiya et al. | 623/1.15 |
| 2002/0077693 A1 | 6/2002 | Barclay et al. | 623/1.13 |
| 2002/0091433 A1 | 7/2002 | Ding et al. | 623/1.2 |
| 2002/0155212 A1 | 10/2002 | Hossainy | 427/2.25 |
| 2002/0183380 A1* | 12/2002 | Hunter | 514/449 |
| 2002/0188323 A1* | 12/2002 | Penner et al. | 607/2 |
| 2003/0065377 A1 | 4/2003 | Davila et al. | 623/1.13 |
| 2003/0099712 A1 | 5/2003 | Jayaraman | 424/486 |
| 2004/0086542 A1* | 5/2004 | Hossainy et al. | 424/423 |
| 2005/0031874 A1* | 2/2005 | Michal et al. | 428/411.1 |
| 2005/0238686 A1* | 10/2005 | Hossainy et al. | 424/423 |
| 2005/0265960 A1* | 12/2005 | Pacetti et al. | 424/78.36 |
| 2005/0288481 A1* | 12/2005 | DesNoyer et al. | 528/310 |
| 2006/0121089 A1* | 6/2006 | Michal et al. | 424/426 |
| 2006/0147412 A1* | 7/2006 | Hossainy et al. | 424/78.27 |
| 2006/0160985 A1* | 7/2006 | Pacetti et al. | 528/272 |
| 2006/0246109 A1* | 11/2006 | Hossainy et al. | 424/426 |
| 2007/0100123 A1* | 5/2007 | Hossainy et al. | 528/272 |

FOREIGN PATENT DOCUMENTS

| | | |
|---|---|---|
| EP | 0 514 406 | 11/1992 |
| EP | 0 604 022 | 6/1994 |
| EP | 0 623 354 | 11/1994 |
| EP | 0 665 023 | 8/1995 |
| EP | 0 701 802 | 3/1996 |
| EP | 0 716 836 | 6/1996 |
| EP | 0 809 999 | 12/1997 |
| EP | 0 832 655 | 4/1998 |
| EP | 0 850 651 | 7/1998 |
| EP | 0 879 595 | 11/1998 |
| EP | 0 910 584 | 4/1999 |
| EP | 0 923 953 | 6/1999 |
| EP | 0 953 320 | 11/1999 |
| EP | 0 970 711 | 1/2000 |
| EP | 0 982 041 | 3/2000 |
| EP | 1 273 314 | 1/2003 |
| JP | 2001-190687 | 7/2001 |
| WO | WO91/12846 | 9/1991 |
| WO | WO95/10989 | 4/1995 |
| WO | WO96/40174 | 12/1996 |
| WO | WO97/10011 | 3/1997 |
| WO | WO97/45102 | 12/1997 |
| WO | WO97/46590 | 12/1997 |
| WO | WO98/17331 | 4/1998 |
| WO | WO98/36784 | 8/1998 |
| WO | WO99/01118 | 1/1999 |
| WO | WO99/38546 | 8/1999 |
| WO | WO99/63981 | 12/1999 |
| WO | WO 00/02599 | 1/2000 |
| WO | WO 00/12147 | 3/2000 |
| WO | WO 00/18446 | 4/2000 |
| WO | WO 00/64506 | 11/2000 |
| WO | WO 00/72893 | * 12/2000 |
| WO | WO 01/01890 | 1/2001 |
| WO | WO 01/15751 | 3/2001 |
| WO | WO 01/17577 | 3/2001 |
| WO | WO 01/45763 | 6/2001 |
| WO | WO 01/49338 | 7/2001 |
| WO | WO 01/74414 | 10/2001 |
| WO | WO 02/03890 | 1/2002 |
| WO | WO 02/026162 | 4/2002 |
| WO | WO 02/34311 | 5/2002 |
| WO | WO 02/056790 | 7/2002 |
| WO | WO 03/000308 | 1/2003 |
| WO | WO 03/022323 | 3/2003 |
| WO | WO 03/028780 | 4/2003 |
| WO | WO 03/037223 | 5/2003 |
| WO | WO 03/039612 | 5/2003 |

OTHER PUBLICATIONS

Anonymous, *Stenting continues to dominate cardiology*, Clinica 720:22 (Sep. 2, 1996), http://www.dialogweb.com/cgi/document?reg=1061848017752, printed Aug. 25, 2003 (2pages).

Aoyagi et al., *Preparation of cross-linked aliphatic polyester and application to thermo-responsive material*, Journal of Controlled Release 32:87-96 (1994).

Barath et al., *Low Dose of Antitumor Agents Prevents Smooth Muscle Cell Proliferation After Endothelial Injury*, JACC 13(2): 252A (Abstract) (Feb. 1989).

Barbucci et al., *Coating of commerically available materials with a new heparinizable material*, J. Biomed. Mater. Res. 25:1259-1274 (Oct. 1991).

Chung et al., *Inner core segment design for drug delivery control of thermo-responsive polymeric micelles*, Journal of Controlled Release 65:93-103 (2000).

Dev et al., *Kinetics of Drug Delivery to the Arterial Wall Via Polyurethane-Coated Removable Nitino Stent: Comparative Study of Two Drugs*, Catheterization and Cardiovascular Diagnosis 34:272-278 (1995).

Dichek et al., *Seeding of Intravascular Stents with Genetically Engineered Endothelial Cells*, Circ. 80(5):1347-1353 (Nov. 1989).

Eigler et al., *Local Arterial Wall Drug Delivery from a Polymer Coated Removable Metalic Stent: Kinetics, Distribution, and Bioactivity of Forskolin*, JACC, 4A (701-1), Abstract (Feb. 1994).

Helmus, *Overview of Biomedical Materials*, MRS Bulletin, pp. 33-38 (Sep. 1991).

Herdeg et al., *Antiproliferative Stent Coatings: Taxol and Related Compounds*, Semin. Intervent. Cardiol. 3:197-199 (1998).

Inoue et al., *An AB block copolymer of oligo(methyl metharcrylate) and poly(acrylic acid) for micellar delivery of hydrophobic drugs*, Journal of Controlled Release 51:221-229 (1998).

Kataoka et al., *Block copolymer micelles as vehicles for drug delivery*, Journal of Controlled Release 24:119-132 (1993).

Levy et al., *Strategies For Treating Arterial Restenosis Using Polymeric Controlled Release-Implants*, Biotechnol. Bioact. Polym. [Proc. Am. Chem. Soc. Symp.], pp. 259-268 (1994).

Liu et al., *Drugs release characteristics of unimolecular polymeric micelles*, Journal of Controlled Release 68:167-174 (2000).

Marconi et al., *Covalent bonding of heparin to a vinyl copolymer for biomedical applications* Biomaterials 18(12):885-890 (1997).

Matsumaru et al., *Embolic Materials For Endovascular Treatment of Cerebral Lesions*, J. Biomater. Sci. Polymer Edn 8(7):555-569 (1997).

Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull. 33(6) 2490-2498 (1985).

Miyazawa et al., *Effects of Pemirolast and Tranilast on Intimal Thickening After Arterial Injury in the Rat*, J. Cardiovasc. Pharmacol., pp. 157-162 (1997).

Nordrehaug et al., *A novel biocompatible coating applied to coronary stents*, European Heart Journal 14, p. 321 (P1694), Abstr. Suppl. (1993).

Ohsawa et al., *Preventive Effects of an Antiallergic Drug, Pemirolast Potassium, on Restenosis After Percutaneous transluminal Coronary Angioplasty*, American Heart Journal 136(6):1081-1087 (Dec. 1998).

Ozaki et al., *New Stent Technologies*, Progress in Cardiovascular Diseases, vol. XXXIX(2):129-140 (Sep./Oct. 1996).

Pechar et al., *Poly(ethylene glycol) Multiblock Copolymer as a Carrier of Anti-Cancer Drug Doxorubicin*, Bioconjucate Chemistry 11(2):131-139 (Mar./Apr. 2000).

Peng et al., *Role of polymers in improving the results of stenting in coronary arteries*, Biomaterials 17:685-694 (1996).

Shigeno, *Prevention of Cerebrovascular Spasm By Bosentan, Novel Endothelin Receptor*, Chemical Abstract 125:212307 (1996).

van Beusekom et al., *Coronary stent coatings*, Coronary Artery Disease 5(7):590-596 (Jul. 1994).

Wilensky et al., *Methods and Devices for Local Drug Delivery in Coronary and Peripheral Arteries*, Trends Cardiovasc. Med. 3(5):163-170 (1993).

Yokoyama et al., *Characterization of physical entrapment and chemical conjugation of adriamycin in polymeric micelles and their design for in vivo delivery to a solid tumor*, Journal of Controlled Release 50:79-92 (1998).

U.S. Appl. No. 09/822,952, filed on Mar. 30, 2001, Charles David Claude.

* cited by examiner

COATINGS FOR IMPLANTABLE MEDICAL DEVICES

BACKGROUND OF THE INVENTION

1. Field of the Invention

This invention relates to the field of medical devices, more particularly, to coatings for devices such as stents.

2. Description of the Background

In the field of medical technology, there is frequently a necessity to administer drugs locally. To provide an efficacious concentration to the treatment site, systemic administration of medication often produces adverse or toxic side effect for the patient. Local delivery is a preferred method in that smaller total levels of medication are administered in comparison to systemic dosages, but are concentrated at a specific site. Thus, local delivery produces fewer side effects and achieves more effective results.

One commonly applied technique for local delivery of a drug is through the use of a polymeric matrix. A polymer impregnated with a drug can be formed into particles or can be coated on implantable medical devices such as stents. Subsequent to the implantation of the particle or the device, the drug slowly elutes from the polymer. A variety of well known polymers have suitable biocompatible properties which allow the polymers to serve as a suitable host for local drug delivery. A selected group of these polymers can also form a film layer or a coating for implantable devices such as stents. One example of a polymer that serves the dual function of being very biocompatible and capable of forming a coating for devices is a copolymer of ethylene and vinyl alcohol, also known as poly(ethylene-co-vinyl alcohol) or EVOH. Poly (ethylene-co-vinyl alcohol) is also known under the trade name EVAL and is distributed commercially by Aldrich Chemical Company of Milwaukee, Wis. EVAL is also manufactured by EVAL Company of America of Lisle, Ill. Other polymers which can be used to coat stents include a copolymer of ethylene with acrylic acid (EAA) and a copolymer of ethylene with glycidyl methacrylate (EGMA).

EVAL is a product of hydrolysis of ethylene-vinyl acetate copolymers. EVAL may also be a terpolymer and may include up to 5% (molar) units derived from styrene, propylene and other suitable unsaturated monomers. EVAL can be described as being hydrophobic and thus is essentially insensitive to moisture. EAA and EGMA, likewise, are hydrophobic and relatively impermeable to gases. The ethylene fragments of EVAL, EAA and EGMA provide hydrophobicity and barrier properties, while functional fragments of each copolymer (hydroxyl groups, carboxyl groups, and glycidyl groups, respectively) provide at least limited solubility in organic solvents.

While EVAL, EAA and EGMA are inert and biocompatible polymers which are quite suitable for use as a drug delivery matrix, and more particularly when used in conjunction with medical devices, some of the properties of these polymers can be improved. In particular, the polymers are prone to protein fouling, which may significantly inhibit the polymers' life time in vivo efficacy.

There is a need for polymeric carriers suitable for the delivery of drugs, and more particularly for coating medical devices used as a means for drug delivery. Suitable characteristics of the polymeric materials should be significantly impermeable to oxygen, high degree of hydrophobicity and long term biocompatibility with minimum protein fouling effects.

SUMMARY

In accordance to one embodiment of the invention, a coating for a medical device, such as a stent, is provided. The coating comprises a biologically compatible compound conjugated to a polymer having the formula

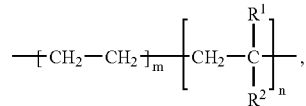

wherein $R^1$ is selected from a group consisting of hydroxyl, carboxyl and an ester group and $R^2$ is selected from a group consisting of hydrogen and an alkyl. The ester group can be a glycidyl group and the alkyl group can be methyl. The biologically compatible compound can be a poly(alkylene glycol)-based compound, a superoxide dismutase compound, a diazenium diolate, or hyaluronic acid. The poly(alkylene glycol)-based compound can be poly(ethylene glycol). In one embodiment, the poly(ethylene glycol) is conjugated to a protein or to a polysaccharide, such as albumin, hyaluronic acid, heparin, heparin derivatives containing a hydrophobic counter-ion or chitosan.

The poly(alkylene glycol)-based compound can contain functional groups such as isocyanate, epoxy, amino, terminal hydroxyl, carboxyl or alkoxy groups. The diazenium diolate can be 1,3-propanediamine, N-{4-[1-(3-aminopropyl)-2-hydroxy-2-nitrosohydrazino]butyl}-diazen-1-ium-1,2-diolate or 1-{N-methyl-N-[6-(N-methylammonio)hexyl] amino}diazen-1-ium-1,2-diolate. The superoxide dismutase compound can be manganese(II)dichloro-aminoethylthiolated pentaazatetracyclohexacosatriene. The coating can further include a therapeutic substance, for example, actinomycin D, taxol, estradiol, rapamycin or structural derivatives or functional analogs thereof.

In accordance with another embodiment of the invention, a method of fabricating a medical device, such as a stent, is provided, comprising forming a coating on the device, the coating comprising a biologically compatible compound conjugated to a polymer having the formula

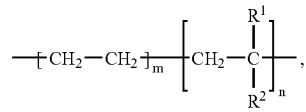

wherein $R^1$ is selected from a group consisting of hydroxyl, carboxyl and an ester group and $R^2$ is selected from a group consisting of hydrogen and an alkyl.

DETAILED DESCRIPTION

This invention provides for modification of polymers to be used for the local delivery of therapeutic substances or drugs. The polymers can also be used as coatings for implantable medical devices such as stents. These polymers are also referred to herein as "modified polymers," "polymers to be modified," or "polymers subject to modification."

The polymers can be characterized by the presence of a polyolefin backbone, pendant on which are alkyl, hydroxyl, and/or carboxyl groups. EVAL is one example of a polymer that can be modified according to this invention. Other examples of polymers that can be modified include a copolymer of ethylene with acrylic acid (EAA) and a copolymer of ethylene with glycidyl methacrylate (EGMA). EVAL, EAA, and EGMA have relatively high oxygen-barrier properties and resistively to water vapor; however, the polymers' long-term biocompatibility is somewhat limited due to protein fouling effects. Modification of the polymers by covalent conjugation to biologically active materials will enhance the polymers' in vivo behavior, thus providing better long-term results.

EVAL, EAA and EGMA can be modified by biologically active compounds, hereinafter also referred to as "modifiers" or "modifying compounds." Modification can be accomplished by covalent conjugation of the polymer to one or more modifiers. The functional groups of the polymers, such as the hydroxyl groups in EVAL, the carboxyl groups in EAA, and the glycidyl groups in EGMA, can be used as the target sites for the conjugation. The modification of the polymer can be conducted directly on the stent or the polymer can be modified first, and the modified product can then applied to the stent.

In one embodiment, the modifiers include poly(ethylene glycol) (PEG) and PEG's functionalized derivatives. More particularly, representative examples include PEG, PEG-isocyanate, PEG-epoxide, and amino-terminated PEG. In accordance with another embodiment of the invention, the modifier can be an intracellular enzyme, for example, oxidoreductases containing seven-coordinate complexes of manganese, which is also known as superoxide dismutase mimics (SODm). In yet another embodiment, the modifier can include diazenium diolate type nitric oxide donors. In yet another embodiment, the modifier can include hyaluronic acids. In yet another embodiment of the invention, the modifying compound(s) can be conjugated to proteins or polysaccharides followed by cold-blending of the conjugates with the matrix polymer such as EVAL.

A therapeutic substance or a drug can be incorporated in the modified polymer. The therapeutic substance can include any compound that exerts a therapeutic or prophylactic effect for the patient. The substance can be for inhibiting the migration and/or proliferation of smooth muscle cells or for the treatment of restenosis and can include small molecule drugs, peptides, proteins, oligonucleotides, or DNA. Examples of the drugs include antiproliferative substances such as actinomycin D, or derivatives and analogs thereof. Synonyms of actinomycin D include dactinomycin, actinomycin IV, actinomycin $I_1$, actinomycin $X_1$, and actinomycin $C_1$. The substance can also fall under the genus of antineoplastic, anti-inflammatory, antiplatelet, anticoagulant, antifibrin, antithrombin, antimitotic, antibiotic, antiallergic and antioxidant substances. Examples of such antineoplastics and/or antimitotics include paclitaxel, docetaxel, methotrexate, azathioprine, vincristine, vinblastine, fluorouracil, doxorubicin hydrochloride, and mitomycin. Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin. Examples of such cytostatic or antiproliferative agents include angiopeptin, angiotensin converting enzyme inhibitors such as captopril, cilazapril or lisinopril, calcium channel blockers (such as nifedipine), colchicine, fibroblast growth factor (FGF) antagonists, fish oil (ω-3-fatty acid), histamine antagonists, lovastatin (an inhibitor of HMG-CoA reductase, a cholesterol lowering drug), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents 1 which may be appropriate include alpha-interferon, genetically engineered epithelial cells, rapamycin, rapamycin derivatives and analogs, and dexamethasone.

The coating of the present invention can be used in conjunction with a balloon-expandable or self-expandable stent. The application of the coating is not limited to stents and the coating can also be used with a variety of other medical devices. Examples of other implantable medical device include stent-grafts, grafts (e.g., aortic grafts), artificial heart valves, cerebrospinal fluid shunts, pacemaker electrodes, axius coronary shunts and endocardial leads (e.g., FINELINE and ENDOTAK, available from Guidant Corporation). The underlying structure of the device can be of virtually any design. The device can be made of a metallic material or an alloy such as, but not limited to, cobalt-chromium alloys (e.g., ELGILOY), stainless steel (316L), "MP35N," "MP20N," ELASTINITE (Nitinol), tantalum, tantalum-based alloys, nickel-titanium alloy, platinum, platinum-based alloys such as, e.g., platinum-iridium alloy, iridium, gold, magnesium, titanium, titanium-based alloys, zirconium-based alloys, or combinations thereof. Devices made from bioabsorbable or biostable polymers can also be used with the embodiments of the present invention. "MP35N" and "MP20N" are trade names for alloys of cobalt, nickel chromium and molybdenum, available from Standard Press Steel Co. of Jenkintown, Pa.

"MP35N" consists of 35% cobalt, 35% nickel, 20% chromium, and 10% molybdenum.

"MP20N" consists of 50% cobalt, 20% nickel, 20% chromium, and 10% molybdenum.

The following examples illustrate various embodiments for the modified polymers.

1. Modification of EVAL

In one embodiment of the invention, EVAL (—[$CH_2$—$CH_2$]$_m$—[$CH_2$—$CH(OH)$]$_n$—) manufactured by EVALCA Corp., Lisle, Ill., has an m:n ratio of 44:56. Those having ordinary skill in the art will understand that EVAL with higher or lower ethylene content can be modified by the same methods as those discussed below. In accordance with some of the embodiments of this invention, EVAL is modified as shown in the following examples.

EXAMPLE 1

Modifier: poly(ethylene glycol)

Poly((ethylene glycol) (PEG) is a highly biologically compatible product. Due to the presence of hydroxyl groups, PEG is capable of entering reactions of condensation with EVAL. The reaction may need to be catalyzed by a suitable acidic or basic catalyst. PEG can be in an oligomeric or polymeric form and can have a molecular weight within a range of between about 500 and about 30,000 Daltons. The conditions under which this reaction is conducted can be determined by one having ordinary skill in the art. EVAL can be firmly bonded to the biologically compatible PEG. Thus, EVAL is modified by PEG and the modified EVAL can have an enhanced long-term biocompatibility.

EXAMPLE 2

Modifier: poly(ethylene glycol)-isocyanate

Poly(ethylene glycol)-isocyanate (hereinafter, PEG-ISO) is a PEG based product having the isocyanate fragments —N=C=O. An example of a PEG-ISO suitable as a modifier for EVAL is a methoxylated PEG-ISO. The PEG-ISO has a general formula $CH_3—[O—CH_2—CH_2]_p—N=C=O$. This modifier, manufactured by Shearwater Corp. of Huntsville, Ala., has a molecular weight of about 5,000 which corresponds to the value of the integer "p" of about 112. Due to the presence of the isocyanate groups, PEG-ISO is chemically very active and readily reacts with EVAL in solution. The —N=C=O group of PEG-ISO, having strong electron accepting properties, reacts with nucleophilic hydroxyl group of EVAL, as illustrated by reaction scheme (I):

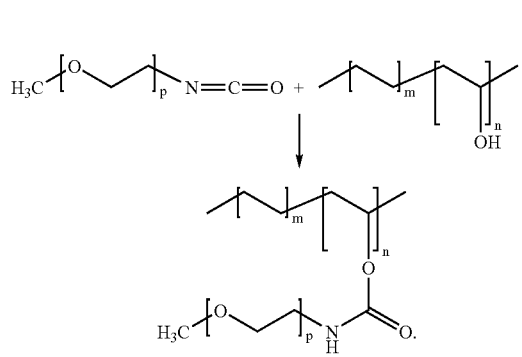
(I)

The conditions under which reaction scheme (I) is conducted can be determined by one having ordinary skill in the art. As a result, EVAL is firmly bonded to the biologically compatible PEG-ISO to form the urethane product of reaction scheme (I). Thus, EVAL, modified by PEG-ISO, can have an enhanced long-term biocompatibility.

EXAMPLE 3

Modifier: poly(ethylene glycol)-epoxide

Poly(ethylene glycol)-epoxide (hereinafter, PEG-EPO) is a PEG-based product having epoxy fragments. An example of a PEG-EPO suitable as a modifier for EVAL is a methoxylated PEG-EPO, such as methoxy-PEG-glycidyl ether and has the following general formula

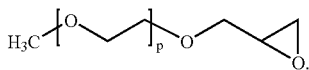

The PEG-EPO has a molecular weight of about 5,000, which corresponds to the value of the integer "p" of about 112, and is manufactured by Shearwater Corp. of Huntsville, Ala.

Epoxy groups in PEG-EPO are reactive, and PEG-EPO easily reacts with EVAL in solution. The epoxy group of PEG-EPO can react with the nucleophilic hydroxyl group of EVAL, via the nucleophilic substitution reaction $S_N2$. Normally, the proton of the hydroxyl group attacks the less substituted α-carbon atom of the epoxy group. The β-carbon is less accessible due to the steric hindrances. As the result of the proton attack on the α-carbon atom, the ring opens and the modified EVAL is formed according to a reaction that can be shown as reaction scheme (II):

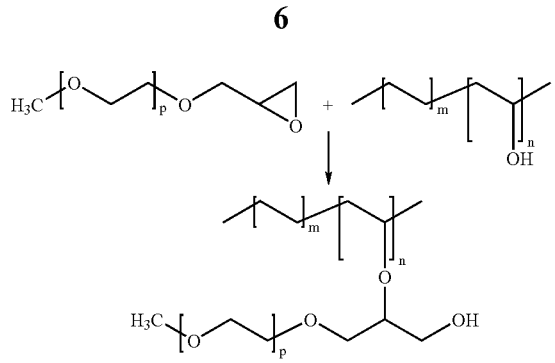

Reaction scheme (II) is carried out more effectively in the presence of electron acceptors, because the electron acceptors facilitate electrophilic polarization of the C—O bond of the epoxy ring, thus making the subsequent attack by the proton of the hydroxyl group of EVAL easier.

Accordingly, modification of EVAL with PEG-EPO is facilitated in the presence of electrophilic ring-opening catalysts, for instance, aprotonic acids such as amine-boron trifluoride adducts or tertiary amines. The use of any ring-opening catalyst is optional. The conditions under which this reaction is conducted can be determined by one having ordinary skill in the art.

EXAMPLE 4

Modifier: Hyaluronic Acid

Hyaluronic acid is a linear polysaccharide composed of disaccharide units of N-acetylglucosamine and D-glucoronic acid. In hyaluronic acid, uronic acid and the aminosugar are linked by alternating β-1,4 and β-1,3 glucosidic bonds. Hyaluronic acid has hydroxymethyl groups and secondary amino groups. EVAL can be modified by these groups. In order to facilitate the reaction of condensation of either the hydroxymethyl groups or the secondary amino groups of hyaluronic acid with the hydroxyl groups of EVAL, an appropriate catalyst may be needed. Alternatively, the modification of EVAL by hyaluronic acid can be carried out in the presence of 1-ethyl-3(3-dimethylaminopropyl) carbodiimide, also known as carbodiimide or EDC, having the formula $CH_3—CH_2—N=C=N—CH_2—CH_2—CH_2—N(CH_3)_2$. EDC is manufactured by Pierce Corp., Rockford, Ill. Instead of EDC, 1,3-dicyclohexylcarbodiimide (DCC) having the formula

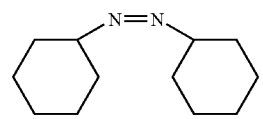

can be used. As a result, EVAL is firmly bonded to the biologically compatible hyaluronic acid for enhanced long term biocompatibility.

EXAMPLE 5

Modifier: Biologically Compatible Compound Conjugated to a Protein and/or Polysaccharide As a first step, a biologically active agent is conjugated to a protein or a polysaccharide, or to a combination of the protein and the polysaccharide. Albumin (also known as albumen or the egg white protein) can be used as the protein, and heparin, heparin derivatives, including the derivatives containing hydrophobic counter-ions, hyaluronic acid or chitosan can be used as polysaccharides. PEG is one example of the biologically active agent to be conjugated to the protein or polysaccharide, or to a combination of the protein and the polysaccharide. Other biologically active agents that can be used include superoxide dismutase-mimetics (SOD-mimetics or SODm) and diazenium diolate type nitric oxide donors.

Superoxide dismutase-mimetics are oxidoreductases based oxidoreductase-based complexes that contain cations of copper, iron, or manganese. SOD-mimetics are major intracellular enzymes that protects the cell against oxygen toxicity by dismutating the radical oxygen superoxide, $—O_2$, to oxygen and hydrogen peroxide.

As a second step, the conjugation of PEG, SODm or diazenium diolates to the protein or polysaccharide, or a combination thereof, is cold-blended with EVAL. As a result, EVAL is modified with a product having high biocompatibility.

Superoxide dismutate-mimetics are oxidoreductases-based complexes that contain cations of copper, iron, or manganese. SOD-mimetics are major intracellular enzymes that protects the cell against oxygen toxicity by dismutating the radical oxygen superoxide, $O_2\%$, to oxygen and hydrogen peroxide.

Manganese-based SODm, manganese(II)dichloro-aminoethylthiolated pentaazatetracyclohexacosatriene (SOD-40470) manufactured by Metaphore Pharmaceuticals, Inc., St. Louis, Mo. is one example of SODm that can be used to conjugate to the protein or polysaccharide. This complex seven-ligand SODm has a formula

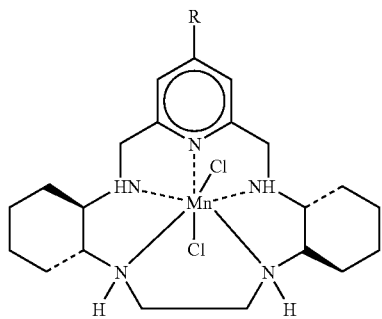

where R is 2-aminoethylmercapto group, $—SCH_2CH_2NH_2$. Those having ordinary skill in the art can also select other types of SODm. Due to the presence of the primary amino ligands, SOD-40470 is chemically quite active and can be easily conjugated to the protein or the polysaccharide, or to a combination of the protein and the polysaccharide.

Diazenium diolate type nitric oxide donors are adducts of nitric oxide (NO) with nucleophilic amines. Diazenium diolates also known as NONOates are highly biologically compatible and possess valuable medicinal properties. In slightly acidic medium they spontaneously release NO which has excellent therapeutical properties. One example of diazenium diolate that can be used to conjugate to the protein or polysaccharide is spermine diazenium diolate (SDD).

An aliphatic NONOate, SDD, or 1,3-propanediamine, N-{4-[1-(3-aminopropyl)-2-hydroxy-2-nitrosohydrazino]butyl}-diazen-1-ium-1,2-diolate has the formula $=NH_2—(CH_2)_3—N[N^+(O)—(N—OH)]—(CH_2)_4—NH—(CH_2)_3—NH_2$ and is manufactured by Molecular Probes, Inc., Eugene, Oreg. Alternatively, other diazenium diolate-type NO donors can be used. One example of a suitable alternative diazenium diolate-type NO donor can be 1-{N-methyl-N-[6-(N-methylammonio)hexyl]amino}diazen-1-ium-1,2-diolate having the formula $CH_3—N^+H_2—(CH_2)_6—N(CH_3—N^+(O^-)=N—O^-$ (MAHMA-NO). Another example of a suitable alternative NONOate can be Z-1-[N-(2-aminoethyl)-N-(2-ammonioethyl)amino]diazen-1-ium-1,2-diolate having the formula $O^-—N^+[N(CH_2—CH_2—NH_2)CH_2—CH_2—N^+H_3]=N—O^-$ (DETA-NO). MAHMA-NO and DETA-NO can be obtained from Cayman Chemical Co., Ann Arbor, Mich.

Due to the presence of amino groups, both SDD, MAHMA-NO and DETA-NO are easily conjugated to the above-mentioned proteins and/or polysaccharides, or to a combination thereof. The conditions under which the reaction of conjugation of PEG, SODm or diazenium diolates to the protein or polysaccharide, or a combination thereof, is conducted can be determined by those having ordinary skill in the art.

As a second step, the conjugated adduct of PEG, SODm or diazenium diolates to the protein or polysaccharid, or a combination thereof, is cold-blended with EVAL. As a result, EVAL is modified with a product having high biocompatibility.

EVAL can be preliminarily derivatized by tosylation (treatment with tosyl chloride), or alternatively by tresylation (by reacting with tresyl chloride). Tosyl chloride is a derivative of toluene, p-toluene sulfonyl chloride having the formula $CH_3—C_6H_4—SO_2Cl$ (TsCl). The process of EVAL derivatization can be conducted directly on the stent. The following process of tosylation can be used.

A 2% (mass) solution of EVAL in dimethylacetamide (DMAC) can be sprayed on the stent and dried for 10 minutes at 80° C., and then for 1 hour at 140° C. A 3% (mass) of TsCl in dry xylene can be prepared and the coated EVAL stent can be shaken for 1 minute with 1.4 ml of the TsCl solution. 0.25 ml of 33% (mass) of pyridine in dry xylene can be added, followed by shaking for 4 hours in a desiccator. The stent can be then rinsed with acetone and twice with 1 mM solution of HCl to remove the excess TsCl. As a result, EVAL can be tosylated according to reaction scheme (III) and the tosyl group is attached to the EVAL backbone via hydroxy group to yield the toluenesulfoester:

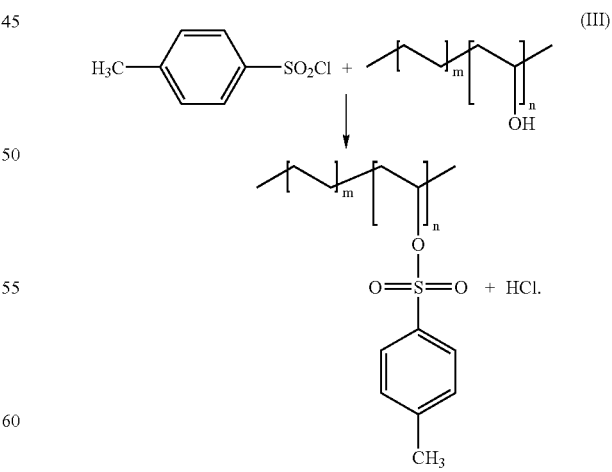

Alternatively, tresyl chloride (2,2,2-trifluoroethanesulphonyl chloride) can be used to derivatrize EVAL, according to reaction scheme (IV) and the tresyl group is attached to the EVAL backbone via hydroxy group:

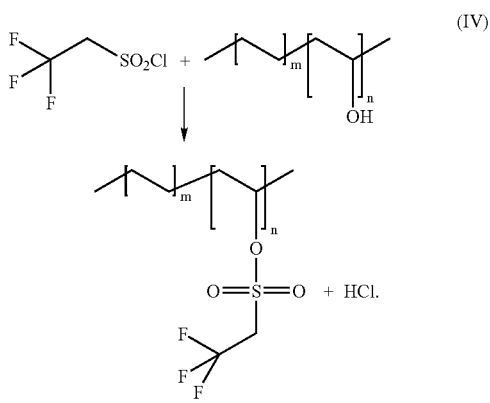

(IV)

EXAMPLE 6

Modifier: Poly(ethylene glycol)-amine Adduct

Poly(ethylene glycol)-amine adduct (hereinafter, PEG-$NH_2$) is a PEG-based product having amino groups $NH_2$. An example of a PEG-$NH_2$ that can be used as a modifier for the tosylated or tresylated EVAL is a methoxylated PEG-$NH_2$ adduct having a general formula $CH_3$—[O—$CH_2$—$CH_2$]$_p$—O—$CH_2$—$CH_2$—$NH_2$. This adduct, manufactured by Shearwater Corp., Huntsville, Ala., has a molecular weight of about 5,000 which corresponds to the value of the integer "p" of about 113.

In addition, since toluenesulfonic acid is known to be a very strong acid, on par with sulfuric or hydrochloric acids, its anion, $CH_3$—$C_6H_4$—$SO_3^-$, is an excellent leaving group in the nucleophilic substitution alkylation reaction of a primary amine, much better than hydroxyl group of underivatized EVAL. Accordingly, the tosylated EVAL obtained as described above, readily reacts with PEG-$NH_2$ as schematically shown by the alkylation reaction scheme (V):

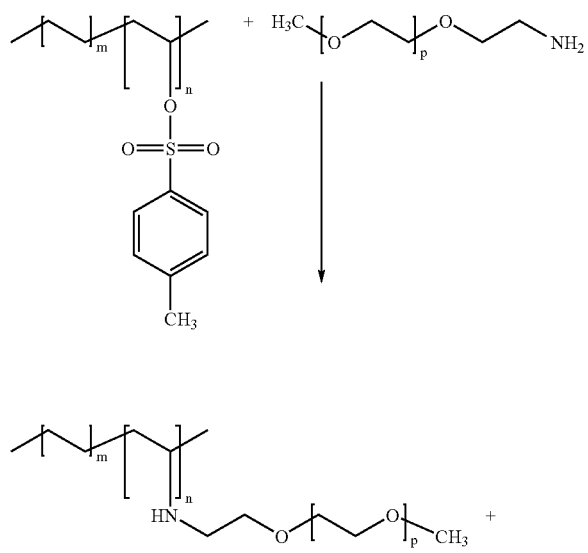

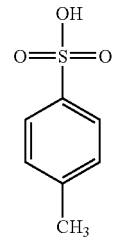

The conditions under which this reaction are conducted can be determined by those having ordinary skill in the art. The reaction of tresylated EVAL and PEG-$NH_2$ is similar to reaction scheme (V). As a result, EVAL is firmly bonded to the biologically compatible PEG-$NH_2$ to form the secondary amine product of reaction (V).

EXAMPLE 7

Modifier: SOD-Mimetic

SOD-mimetics are highly biocompatible and can be used for modifying tosylated or tresylated EVAL. In particular, SOD-40470 can be used as a modifying agent for the tosylated or tresylated EVAL. Due to the presence of the primary amino ligands, SOD-40470 is chemically active and is readily alkylated with the tosylated or tresylated EVAL in solution. Alternatively, other SOD-mimetics can be used so long as they have amino groups. The mechanism of the tosylation or tresylation is via a reaction of alkylation of the amino group of SODm and is similar to reaction scheme (V) discussed above. The conditions under which this reaction is conducted will be determined by those having ordinary skill in the art. As a result, EVAL is firmly bonded to the biologically compatible amino ligand-containing SODm to form the secondary amine product.

EXAMPLE 8

Modifier: Spermine Diazenium Diolate

Tosylated or tresylated EVAL can be modified by binding it to a NONOate. Spermine diazenium diolate, SDD, can be used as a modifying agent for the tosylated or tresylated EVAL. Due to the presence of two primary and one secondary amino groups, SDD is easily alkylated with the tosylated or tresylated EVAL in solution. The mechanism of such tosylation or tresylation is via a reaction of alkylation of the amino group of SDD and is similar to reaction scheme (V) discussed above. Alternatively, other diazenium diolate-type NO donors can be used, so long as they have amino groups, for example, MAHMA-NO or DETA-NO. The mechanism of binding of the tosylated or tresylated EVAL to MAHMA-NO or DETA-NO is the same as the mechanism of binding to SDD.

The conditions under which the reaction of binding the tosylated or tresylated EVAL to SDD, or the alternative diazenium diolate-type NO donors, is conducted can be determined by those having ordinary skill in the art. As a result, EVAL is firmly bonded to the biologically compatible diazenium diolate-type NO donors to form the secondary amine product. Since the modified product will be able to release NO having valuable medicinal properties, the stent coating will acquire additional therapeutic properties.

3. Polymer Subject to Modification is a Copolymer of Ethylene with Acrylic Acid (EAA)

EAA has the general formula —[$CH_2$—$CH_2$]$_m$—[$CH_2$—CH(COOH)]$_n$—. In one embodiment of this invention, 25% (by mass) aqueous, ammonia-neutralized dispersion of EAA manufactured by Michelman, Inc., Cincinnati, Ohio is used. In some of the embodiments of this invention EAA is modified as illustrated in the following examples.

EXAMPLE 9

Modifier: PEG-$NH_2$

Due to the presence of the amino groups, PEG-$NH_2$ is chemically active and is readily acylated with the carboxyl groups of EAA. Accordingly, EAA readily reacts with PEG-$NH_2$. The reaction is carried out in the presence of EDC. EAA reacts with EDC and forms an O-acylisourea, an amine-reactive intermediate. This intermediate is unstable in aqueous environment and immediately reacts with PEG-$NH_2$ through PEG-$NH_2$'s amino groups.

The path of the reaction is via the nucleophilic attack of the carbon of the carboxyl group of EAA by the electron-rich nitrogen of the amino group of PEG-$NH_2$, followed by the formation of the peptide bond —NH—CO—. Water is the by-product. The process is schematically shown by the acylation reaction scheme (VI):

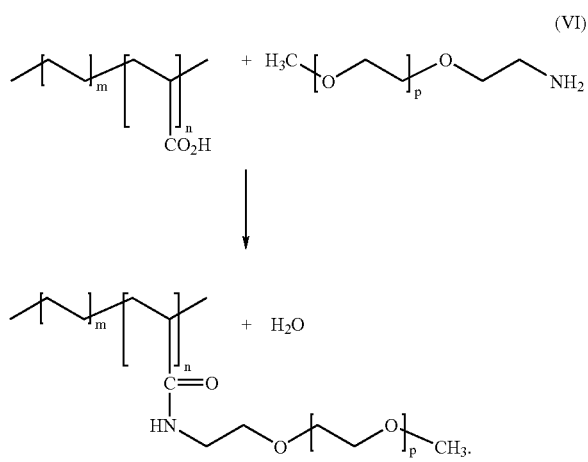

Reaction scheme (VI) shows only the final products of the process. The intermediate stage of the formation of O-acylisourea is omitted. The conditions under which reaction scheme (VI) is conducted can be determined by those having ordinary skill in the art. As a result, EAA is firmly bonded to the biologically compatible PEG-$NH_2$ to form the peptide-type product of reaction scheme (VI).

EXAMPLE 10

Modifier: SOD-Mimetic

SOD-40470 can be used as a modifying agent of EAA. Due to the presence of the primary amino ligands, SOD-40470 is chemically active and readily couples with EAA. Just as in the case of modification with PEG-$NH_2$, the reaction is carried in the presence of EDC. The mechanism of the reaction is via acylation of the amino group of SOD-40470 and is similar to reaction scheme (VI). Other SOD-mimetics can be used so long as they have amino groups. EAA can be firmly bonded to the biologically compatible amino ligand-containing SOD-40470 to form the peptide-type product.

EXAMPLE 11

Modifier: Spermine Diazenium Diolate

SDD can be used as a modifying agent of EAA. Due to the presence of the amino groups, SDD is chemically active and readily couples with EAA. Just as in the case of modification with PEG-$NH_2$ and SOD-40470, the reaction is carried out in the presence of EDC. The mechanism of the reaction is via acylation of the amino group of SDD and is similar to reaction scheme (VI). Other diazenium diolate-type NO donors can be used, so long as they have amino groups, for example, MAHMA-NO or DETA-NO. The mechanism of coupling the EAA to MAHMA-NO or to DETA-NO is the same as the mechanism of coupling the EAA to SDD. The conditions under which the reaction of binding EAA to SDD or the alternative diazenium diolate-type NO donors is conducted can be determined by those having ordinary skill in the art. As a result, EAA is firmly bonded to the biologically compatible diazenium diolate-type NO donors to form the peptide-type adduct. The modified product will be able to release NO.

4. Polymer Subject to Modification is a Copolymer of Ethylene with Glycidyl Methacrylate (EGMA)

EGMA has the general formula

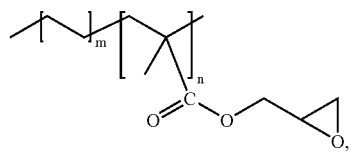

wherein m and n are integers. A brand of EGMA having about 80% (by mass) of the units derived from ethylene can be used for modification. EGMA is an aliphatic epoxy oligomer with relatively high contents of epoxy functionality. Due to the presence of the epoxy groups, EGMA is chemically reactive and can be modified via these epoxy groups, particularly, by reacting EGMA with substances containing amino-, carboxyl-, and/or hydroxyl groups. In accordance with some of the embodiments of this inventions EGMA is modified as shown in the following examples.

EXAMPLE 12

Modifier: PEG-$NH_2$

As mentioned above, PEG-$NH_2$ is chemically active and its amino group easily reacts with the epoxy group of EGMA. The path of the reaction is via the $S_N2$ nucleophilic attack of the epoxy group of EGMA by the electron-rich nitrogen of the amino group of PEG-$NH_2$. As a result, the oxirane ring of EGMA opens and a hydroxyl group forms. The process is schematically shown by reaction scheme (VII):

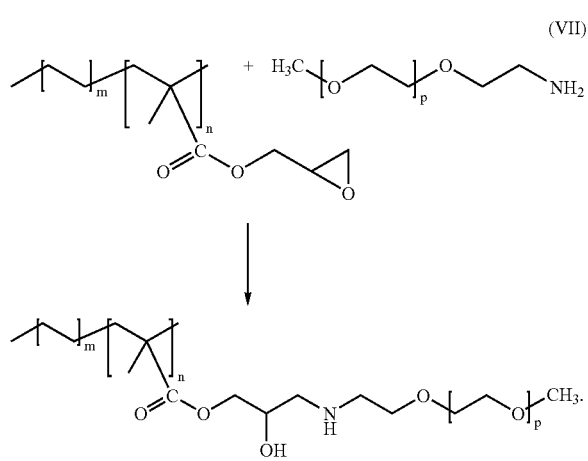

(VII)

Reaction scheme (VII) may then continue and, depending on the amounts of EGMA and PEG-$NH_2$, the second proton of the amino group of the adduct formed according to reaction (VII) can attack the second molecule of EGMA by the same nucleophilic mechanism as shown by reaction (VII). As a result a cross-linked oligomer may form. The conditions under which reaction (VII) is conducted can be determined by those having ordinary skill in the art. Irrespective of whether the reaction stops at a stage shown by reaction (VII) or continues through the formation of the cross-linked tri-dimensional oligomeric network, EGMA is firmly bonded to the biologically compatible PEG-$NH_2$.

EXAMPLE 13

Modifier: SOD-Mimetic

SOD-40470 can be used as a modifying agent of EGMA. Due to the presence of the primary amino ligands, SOD-40470 is chemically active and readily couples with EGMA. The mechanism of the reaction is via nucleophilic bonding of the amino group of SOD-40470 to the oxirane group of EGMA and is similar to the reaction (VII) discussed above. Alternatively, other SOD-mimetics can be used so long as they have amino groups. EGMA can be firmly bonded to the biologically compatible amino ligand-containing SOD-40470 to form a linear or cross-linked oligomer, depending on the conditions of the reaction of modification.

EXAMPLE 14

Modifier: Spermine Diazenium Diolate

SDD can be used as a modifying agent of EGMA. Due to the presence of the amino groups, SDD is chemically active and readily couples with EGMA according to the mechanism similar to reaction scheme (VII). Other diazenium diolate-type NO donors can be used, so long as they have amino groups, for example, MAHMA-NO or DETA-NO. The mechanism of coupling the EAA to MAHMA-NO or DETA-NO is the same as the mechanism of coupling to the EAA to SDD. The conditions under which the reaction of binding EGMA to SDD, or the alternative diazenium diolate-type NO donors, is conducted can be determined by those having ordinary skill in the art. EGMA can be firmly bonded to the biologically compatible diazenium diolate-type NO donors.

EXAMPLE 15

Modifier: Hydroxyl-Terminated Methoxy-PEG

Hydroxyl-terminated methoxy-PEG is a PEG-based product having hydroxyl groups. An example of a hydroxyl-terminated methoxy-PEG suitable as a modifier for EGMA is monomethyl ether of PEG, a methoxylated PEG adduct having a general formula $CH_3O-[CH_2-CH_2-O]_p-CH_2-CH_2-OH$, known as a low-diol mPEG. The adduct is manufactured by Shearwater Corp., Huntsville, Ala., and, like PEG-ISO or PEG-EPO, has a molecular weight of about 5,000, which corresponds to a value of the integer "p" of about 112. The low-diol mPEG is a strong nucleophilic agent and bonds with EGMA via a nucleophilic substitution reaction of its nucleophilic hydroxyl group with the oxirane ring of EGMA. The mechanism of that reaction is similar to the mechanism illustrated schematically by reaction (II).

Carboxyl-terminated methoxy-PEG is a PEG-based product having carboxyl groups, —COOH. An example of a carboxyl-terminated methoxy-PEG suitable as a modifier for EGMA is methoxy-PEG propionic acid, a methoxylated PEG-based adduct having a general formula $CH_3O-[CH_2-CH_2-O]_p-CH_2-CH_2COOH$, known as PA-PEG. The adduct, manufactured by Shearwater Corp., Huntsville, Ala., has a molecular weight of about 5,000 which corresponds to the value of the integer "p" of about 111.

Naturally, modification of EGMA by the low diol mPEG is carried out more effectively in the presence of the electron acceptors, which facilitate the nucleophilic attack of the epoxy group of EGMA by the proton of the hydroxyl group of the low diol mPEG. Accordingly, modification of EGMA with the low diol mPEG is facilitated in the presence of ring-opening catalysts, that include either amines or electrophilic agents, for example, aprotonic acids such as amine-boron trifluoride adducts. The use of any ring-opening catalysts is optional.

The conditions under which this reaction is conducted can be determined by those having ordinary skill in the art. As a result, EGMA is firmly bonded to the biologically compatible low diol mPEG to form the product similar to the product of reaction (II).

EXAMPLE 16

Modifier: Carboxyl-Terminated Methoxy-PEG

A methoxylated PEG-based adduct having a general formula $CH_3O-[CH_2-CH_2-O]_n-CH_2-CH_2COOH$, known as PA-PEG, can be used. The adduct, manufactured by Shearwater Corp., Huntsville, Ala., has a molecular weight of about 5,000 which corresponds to the value of the integer "n" of about 111.

Like low diol mPEG, PA-PEG is a strong nucleophilic agent which can react with the epoxy group of EGMA. The mechanism of this reaction is similar to the mechanism illustrated schematically by reaction (II), except that a proton of a carboxyl group carries out the nucleophilic attack instead of the alcohol proton illustrated by reaction (II). EGMA can be firmly bonded to the biologically compatible PA-PEG to form a product similar to the product of reaction (II).

Modification of EVAL, tosylated or tresylated EVAL, EAA and EGMA discussed in Examples 1–16 can be recapitulated as shown in Table 1.

TABLE 1

| Example | The modified polymer | The modifying agent |
| --- | --- | --- |
| 1 | EVAL | PEG |
| 2 | EVAL | PEG-ISO |
| 3 | EVAL | PEG-EPO |
| 4 | EVAL | Hyaluronic acid |
| 5 | EVAL | PEG or SODm or diazenium diolate + albumin or heparin or chitosan |
| 6 | Tosylated or tresylated EVAL | PEG-NH$_2$ |
| 7 | Tosylated or tresylated EVAL | SODm |
| 8 | Tosylated or tresylated EVAL | SDD |
| 9 | EAA | PEG-NH$_2$ |
| 6 | Tosylated or tresylated EVAL | PEG-NH$_2$ |
| 7 | Tosylated or tresylated EVAL | SODm |
| 8 | Tosylated or tresylated EVAL | SDD |
| 9 | EAA | PEG-NH$_2$ |
| 10 | EAA | SODm |
| 11 | EAA | SDD |
| 12 | EGMA | PEG-NH$_2$ |
| 13 | EGMA | SODm |
| 14 | EGMA | SDD |
| 15 | EGMA | Low diol mPEG |
| 16 | EGMA | PA-PEG |

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A coating for a medical device, wherein the coating comprises a biologically compatible compound conjugated to a polymer,
   wherein the polymer comprises tosylated or tresylated ethylene-vinyl alcohol copolymer (EVAL), or ethylene-glycidyl methacrylate copolymer (EGMA), and
   wherein the biologically compatible compound comprises a superoxide dismutase compound.

2. The coating of claim 1, wherein the superoxide dismutase compound comprises manganese(II)dichloro-aminoethylthiolated pentaazatetracyclohexacosatriene.

3. The coating of claim 1, wherein the device comprises a stent.

4. The coating of claim 1, wherein the biologically compatible compound is further conjugated to a protein or a polysaccharide.

5. The coating of claim 1 further comprising a therapeutic substance, wherein the therapeutic substance is estradiol, paclitaxel, docetaxel or rapamycin.

6. A coating for a medical device, wherein the coating comprises a biologically compatible compound conjugated to a polymer, wherein the polymer comprises tosylated or tresylated ethylene-vinyl alcohol copolymer (EVAL), or ethylene-glycidyl methacrylate copolymer (EGMA), and
   wherein the biologically compatible compound comprises a diazenium diolate compound.

7. The coating of claim 6, wherein the diazenium diolate comprises a component selected from a group consisting of 1,3-propanediamine, N-{4-[1-(3-aminopropyl)-2-hydroxy-2-nitrosohydrazino]butyl}-diazen-1-ium-1,2-diolate and 1-{N-methyl-N-[6-(N-methylammonio)hexyl] amino}diazen-1-ium-1,2-diolate.

8. The coating of claim 6, wherein the device comprises a stent.

9. The coating of claim 6, wherein the biologically compatible compound is further conjugated to a protein or to a polysaccharide.

10. The coating of claim 6 further comprising a therapeutic substance, wherein the therapeutic substance is estradiol, paclitaxel, docetaxel, or rapamycin.

11. A method of fabricating a medical device comprising:
    (a) modifying a polymer by reacting a biologically compatible compound with the polymer, wherein the polymer comprises tosylated or tresylated ethylene-vinyl alcohol copolymer (EVAL), or ethylene-glycidyl methacrylate copolymer (EGMA), and
    (b) depositing the polymer on an implantable medical device;
    wherein the biologically compatible compound comprises a superoxide dismutase compound.

12. The method of claim 11, wherein the superoxide dismutase compound comprises manganese(II)dichloro-aminoethylthiolated pentaazatetracyclohexacosatriene.

13. The method of claim 11, wherein the biologically compatible compound further comprises a diazenium diolate or hyaluronic acid.

14. The method of claim 11, wherein the device comprises a stent.

15. The method of claim 11, wherein the superoxide dismutase compound comprises manganese(II)dichloro-aminoethylthiolated pentaazatetracyclohexacosatriene.

16. The method of claim 11 further comprising a therapeutic substance, wherein the therapeutic substance is estradiol, paclitaxel, docetaxel, or rapamycin.

17. A method of fabricating a medical device comprising:
    (a) modifying a polymer by reacting a biologically compatible compound with the polymer, wherein the polymer comprises tosylated or tresylated ethylene-vinyl alcohol copolymer (EVAL), or ethylene-glycidyl methacrylate copolymer (EGMA), and
    (b) depositing the polymer on an implantable medical device; wherein the biologically compatible compound comprises a diazenium diolate compound.

18. The method of claim 9, wherein the diazenium diolate comprises a component selected from a group consisting of 1,3-propanediamine, N-{4-[1-(3-aminopropyl)-2-hydroxy-2-nitrosohydrazino]butyl}-diazen-1-ium-1,2-diolate and 1-{N-methyl-N-[6-(N-methylammonio)hexyl] amino}diazen-1-ium-1,2-diolate.

19. The method of claim 17, wherein the biologically compatible compound further comprises a polysaccharide comprising a component selected from a group consisting of heparin, heparin containing hydrophobic counter-ion, chitosan, and hyaluronic acid.

20. The method of claim 19, wherein the therapeutic substance is taxol, estradiol, paclitaxel, docetaxel, or rapamycin.

21. The method of claim 17, wherein the biologically compatible compound is further conjugated to a protein or a polysaccharide.

22. The method of claim 17 further comprising a therapeutic substance, wherein the therapeutic substance is estradiolg paclitaxel, docetaxel, or rapamycin.

23. A method of fabricating a medical device comprising:
    (a) forming a polymeric coating on an implantable medical device, wherein the polymer comprises tosylated or tresylated ethylene-vinyl alcohol copolymer (EVAL), or ethylene- glycidyl methacrylate copolymer (EGMA), and (b) modifying the coating by reacting the polymer with a biologically compatible compound, wherein the biologically compatible compound comprises a superoxide dismutase compound.

24. The method of claim 14, wherein the device comprises a stent.

25. The method of claim 23, further comprising a therapeutic substance contained in the coating wherein the therapeutic substance is estradiol, paclitaxel, docetaxel, or rapamycin.

26. The method of claim 23, wherein the device comprises a stent.

27. The method of claim 23, wherein the biologically compatible compound is further conjugated to a protein or a polysaccharide.

28. A method of fabricating a medical device comprising:
(a) forming a polymeric coating on an implantable medical device, wherein the polymer comprises tosylated or tresylated ethylene-vinyl alcohol copolymer (EVAL), or ethylene- glycidyl methacrylate copolymer (EGMA), and
(b) modifying the coating by reacting the polymer with a biologically compatible compound, wherein the biologically compatible compound comprises a diazenium diolate compound.

29. The method of claim 16, wherein the biologically compatible compound is conjugated to a protein or a polysaccharide.

30. The method of claim 28, wherein the device comprises a stent.

31. The method of claim 28 further comprising a therapeutic substance contained in the coating wherein the therapeutic substance is estradiol, paclitaxel, docetaxel, or rapamycin.

32. The method of claim 28, wherein the biologically compatible compound is further conjugated to a protein or a polysaccharide.

33. A method of fabricating a medical device comprising forming a coating on the device, wherein the coating comprises a biologically compatible compound conjugated to a polymer comprising tosylated or tresylated ethylene-vinyl alcohol copolymer (EVAL) or ethylene-glycidyl methacrylate copolymer (EGMA)
wherein the biologically compatible compound comprises a superoxide dismutase compound, a diazenium diolate, or hyaluronic acid; and,
wherein the diazenium diolate comprises a component selected from a group consisting of 1,3-propanediamine, N- {4-[1-(3-aminopropyl)-2-hydroxy-2-nitrosohydrazino] butyl}-diazen-1-ium-1,2-diolate and 1-{N-methyl-N-[6-(N-methylammonio)hexyl] amino}diazen-1-ium- 1,2-diolate.

34. The coating of claim 1 further comprising a therapeutic substance.

35. The coating of claim 3 further comprising a therapeutic substance.

36. The method of claim 34, wherein the biologically compatible compound is further conjugated to a protein or a polysaccharide.

37. The method of claim 34 further comprising a therapeutic substance, wherein the therapeutic substance is estradiol, paclitaxel, docetaxel, or rapamycin.

38. The method of claim 30, wherein the medical device comprises a stent.

39. The method of claim 33, wherein the biologically compatible compound is further conjugated to a protein or a polysaccharide.

40. The method of claim 33 further comprising a therapeutic substance, wherein the therapeutic substance is estradiol, paclitaxel, docetaxel, or rapamycin.

41. A coating for a medical device, wherein the coating comprises a biologically compatible compound conjugated to a polymer comprising tosylated or tresylated ethylene-vinyl alcohol copolymer (EVAL), or ethylene-glycidyl methacrylate copolymer (EGMA),
wherein the biologically compatible compound comprises a superoxide dismutase compound, a diazenium diolate, or hyaluronic acid; and
wherein the diazenium diolate comprises a component selected from a group consisting of 1,3-propanediamine, N-{4-[1-(3-aminopropyl)-2-hydroxy-2-nitrosohydrazino]butyl}-diazen 1-ium- 1,2-diolate and 1-{N-methyl-N-[6-(N-methylammonio)hexyl]amino}diazen- 1-ium 1,2-diolate.

42. The method of claim 30, wherein the biologically compatible compound is conjugated to a protein or a polysaccharide.

43. The coating of claim 42, wherein the medical device comprises a stent.

44. The method of claim 32, wherein the biologically compatible compound is conjugated to a protein or a polysaccharide.

45. The coating of claim 42 further comprising a therapeutic substance,
wherein the therapeutic substance is estradiol, paclitaxel, docetaxel, or rapamycin.

46. The method of claim 30 further comprising a therapeutic substance.

47. The coating of claim 31 further comprising a therapeutic substance.

48. The coating of claim 41 further comprising a therapeutic substance,
wherein the therapeutic substance is estradiol, paclitaxel, docetaxel, or rapamycin.

* * * * *